United States Patent [19]

Browne

[11] Patent Number: 4,617,307

[45] Date of Patent: Oct. 14, 1986

[54] SUBSTITUTED IMIDAZO[1,5-A]PYRIDINE DERIVATIVES AS AROMATASE INHIBITORS

[75] Inventor: Leslie J. Browne, Morris Plains, N.J.

[73] Assignee: Ciba-Geigy Corporation, Ardsley, N.Y.

[21] Appl. No.: 622,421

[22] Filed: Jun. 20, 1984

[51] Int. Cl.[4] .................... A61K 31/44; C07D 471/04
[52] U.S. Cl. .................................. 514/300; 546/121
[58] Field of Search ...................... 546/121; 424/256; 514/300

[56] References Cited

U.S. PATENT DOCUMENTS

| | | | |
|---|---|---|---|
| 3,790,586 | 2/1974 | Irikura et al. | 546/121 |
| 4,361,567 | 11/1982 | Bristol et al. | 546/121 X |
| 4,409,226 | 10/1983 | Bristol et al. | 544/127 X |
| 4,444,775 | 4/1984 | Ford | 424/256 |
| 4,470,986 | 9/1984 | Browne | 546/121 X |

FOREIGN PATENT DOCUMENTS

| | | | |
|---|---|---|---|
| 15171 | 9/1980 | European Pat. Off. | 546/121 |
| 114573 | 8/1984 | European Pat. Off. | 546/121 |

OTHER PUBLICATIONS

Morrison and Boyd, "Organic Chemistry", 2nd Ed., Allyn and Bacon, Inc., Boston, 1966.
Fuentes and Paudler, J. Org. Chemistry, 40, 1210 (1975).
Houben-Weyl, Methoden der Organischen Chemie, Thieme Stuttgart, 1952, vol. VIII.
R. Graf, Angewandte Chemie, vol. 80, 183 (1968).
D. T. Moury, Chem. Rev. 42, 251 (1948).
P. Blatcher et al., *Tetrahedron Letters*, 21, 2195 (1980).
G. Durant et al., *J. Med. Chem.*, 16, 1272 (1973).

*Primary Examiner*—Richard A. Schwartz
*Attorney, Agent, or Firm*—Norbert Gruenfeld

[57] ABSTRACT

Compounds of the formula

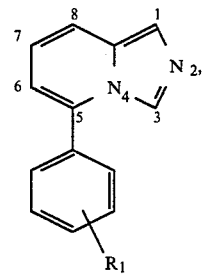

(Ia)

wherein $R_1$ represents cyano, nitro or $C_1$–$C_4$-alkyl or the 7,8-dihydro derivative thereof or the 5,6,7,8 tetrahydro derivative of the formula

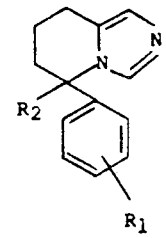

(Ib)

wherein $R_1$ is as defined under formula Ia and $R_2$ is hydrogen, $C_1$–$C_4$-alkyl, halogen etherified or esterified hydroxy or mercapto, carboxy-$C_1$–$C_4$-alkyl or $C_1$–$C_4$-alkoxycarbonyl-$C_1$–$C_4$-alkyl or $C_1$–$C_4$-alkanoyl, to stereoisomers, mixtures of these stereoisomers and salts of these compounds are disclosed as well as their preparation, pharmaceutical compositions containing the same and the use thereof as inhibitors of aromatase activity.

20 Claims, No Drawings

SUBSTITUTED IMIDAZO[1,5-A]PYRIDINE DERIVATIVES AS AROMATASE INHIBITORS

The invention relates to novel substituted imidazo[1,5-a]pyridine derivatives which have valuable pharmacological properties as aromatase inhibitors, to pharmaceutical compositions containing the novel compound, to the use of these compounds as medicaments, for example in a method for treating estrogen dependent diseases, for example female breast cancer, by administration of an effective amount of said compounds or compositions to mammals including man, and to processes for preparing these compounds, to intermediates and to processes for preparing these intermediates.

Particularly, the invention relates to a compound of the formula

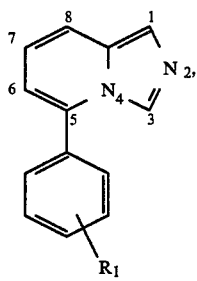

(Ia)

wherein $R_1$ represents cyano, nitro or $C_1$–$C_4$-alkyl, the 7,8-dihydro derivative thereof or the 5,6,7,8-tetrahydro derivative of the formula

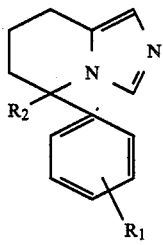

(Ib)

wherein $R_1$ is as defined under formula Ia and $R_2$ is hydrogen, $C_1$–$C_4$-alkyl, aryl-$C_1$–$C_4$-alkyl, halogen, etherified or esterified hydroxy or mercapto, carboxy-$C_1$–$C_4$-alkyl, $C_1$–$C_4$-alkoxycarbonyl-$C_1$–$C_4$-alkyl or $C_1$–$C_4$-alkanoyl, to stereoisomers, mixtures of these stereoisomers and salts of these compounds, to pharmaceutical compositions that contain these compounds, to the use of these compounds as medicaments, to the manufacture of pharmaceutical compositions, and to processes for the manufacture of these compounds.

In the specification of the present ivnention, the term "lower", which is used in connection with groups or radicals, for example lower alkyl, lower alkylene, lower alkoxy, lower alkanoyl etc., means that, unless expressly defined otherwise, the groups or radicals so designated contain up to and including 7, and preferably up to and including 4, carbon atoms.

The 5,6,7,8-derivatives of the formula Ib have a chiral C-atom in the 5-position. The 5R- and the 5S-enantiomers as well as the 5(R,S)-racemate fall within the scope of the present invention.

The generic terms used in the specification of the invention preferably are defined as follows:

$C_1$–$C_4$-Alkyl $R_1$ or $R_2$ is, for example, ethyl, n-propyl, isopropyl, n-butyl, sec-butyl, or tert-butyl and preferably methyl.

Halogen $R_2$ is, for example, fluoro or bromo or, preferably, chloro.

Aryl-$C_1$–$C_4$-alkyl is, for example, benzyl.

Etherified hydroxy or mercapto $R_2$ is, for example, a hydroxy or mercapto group which is etherified by $C_1$–$C_4$-alkyl, for example methyl or ethyl, aryl-$C_1$–$C_4$-alkyl, for example benzyl, 2-phenylethyl or diphenylmethyl, or aryl, for example phenyl.

Etherified hydroxy or mercapto $R_2$ is, preferably, $C_1$–$C_4$-alkoxy, for example methoxy or ethoxy, $C_1$–$C_4$-alkylthio, for example methyl- or ethylthio, aryl-$C_1$–$C_4$-alkylthio, for example benzylthio, 2-phenylethylthio or diphenylmethylthio, or is arylthio, for example phenylthio.

Esterified hydroxy or mercapto $R_2$ is, for example, a hydroxy or mercapto group which is esterified by acyl, for example $C_1$–$C_4$-alkanoyl, for example formyl or acetyl.

Carboxy-$C_1$–$C_4$-alkyl $R_2$ is, for example, carboxymethyl or 2-carboxyethyl.

$C_1$–$C_4$-Alkoxycarbonyl-$C_1$–$C_4$-alkyl $R_2$ is, for example methoxy- or ethoxycarbonylmethyl.

$C_1$–$C_4$-Alkanoyl $R_2$ is, for example, formyl, acetyl or propionyl.

The compounds of the formula Ia and Ib form acid addition salts with acids, particularly pharmaceutically acceptable salts with conventional acids for example mineral acids, for example hydrochloric acid, sulfuric or phosphoric acid, or organic acids, for example aliphatic or aromatic carboxylic or sulfonic acids, e.g. formic, acetic, propionic, succinic, glycolic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, toluenesulfonic, naphthalenesulfonic, sulfanilic or cyclohexylsulfamic acid. Salts may also be formed with amino acids, such as arginine and lysine.

The invention especially relates to a compound of the formula Ia, wherein $R_1$ represents cyano, or the 7,8-dihydro derivative thereof, or the 5,6,7,8-tetrahydro derivative of the formula Ib, wherein $R_1$ is cyano and $R_2$ is hydrogen, $C_1$–$C_4$-alkyl, for example methyl or ethyl, $C_1$–$C_4$-alkoxy, for example methoxy or ethoxy, $C_1$–$C_4$-alkylthio, for example methyl- or ethylthio, aryl-$C_1$–$C_4$-alkylthio, for example benzylthio, 2-phenylethylthio or diphenylmethylthio, arylthio, for example phenylthio, or $C_1$–$C_4$-alkanoyl, for example formyl, acetyl, and pharmaceutically acceptable acid addition salts of a compound of the formula Ia or Ib.

The invention preferably relates to a compound of the formula

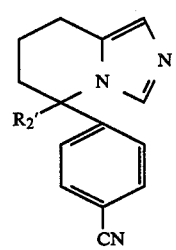

(Ic)

wherein $R_2'$ is hydrogen, $C_1$-$C_4$-alkyl, for example methyl or ethyl, $C_1$-$C_4$-alkoxy, for example methoxy or ethoxy, $C_1$-$C_4$-alkylthio, for example methyl- or ethylthio, aryl-$C_1$-$C_4$-alkylthio, for example benzylthio, 2-phenylethylthio or diphenylmethylthio, arylthio, for example phenylthio, or $C_1$-$C_4$-alkanoyl, for example formyl or acetyl, and pharmaceutically acceptable acid addition salts of this compound.

Most preferred is the compound of the formula Ic, wherein $R_2'$ is hydrogen and pharmaceutically acceptable acid addition salts of this compound.

The compounds of the instant invention have valuable pharmacological properties for example by inhibiting aromatase activity in mammals, including humans. For example, these compounds inhibit the metabolic conversion of androgens to estrogens. Thus, the compounds of formula I are useful in the treatment of gynecomastia, i.e., male breast development, by inhibiting the aromatization of steroids in males susceptible to this condition. Moreover, the compounds of formula I are useful in the treatment of estrogen dependent diseases, including estrogen dependent breast cancer, especially in postmenopausal females, by inhibiting estrogen synthesis.

These effects are demonstrable in in vitro assay tests or in vivo animal tests using advantageously mammals, e.g. guinea pigs, mice, rats, cats, dogs, or monkeys.

The in vitro inhibition of aromatase acitivity of the compounds of the present invention can be demonstrated as follows:

A microsomal fraction is prepared from fresh term human placentas by the method described by Thompson and Siiteri, J. Biol. Chem., Vol. 249, p. 5364 (1974). The microsomal preparation so obtained is lyophilized and stored at $-40°$ C. in a dessicator.

The assay is performed in a total volume of 1 ml of 0.05M potassium phosphate buffer (pH 7,4) at 37° C. The incubation mixture contains $1.135 \times 10^{-7}$M [4-$^{14}$C]-androstene-3,17-dione (New England Nuclear, SA 59.7 mCi/mmole), $2.4 \times 10^{-4}$M NADPH (Sigma, tetrasodium salt Type III), varying concentrations of 5-p-cyanophenyl-5,6,7,8-tetrahydroimidazo[1,5-a]pyridine as representative test compound and 226 $\mu$g/ml of the microsomal enzyme preparation, which is equivalent to 120 $\mu$g of microsomal protein as determined by the method of Lowry et al., J. Biol. Chem., Vol. 193, p. 265 (1951). After 20 minutes of incubation the mixture is extracted twice with 7 volumes of ethyl acetate, and the combined extracts are evaporated to dryness. The resulting residue is separated by chromatography for 65 minutes on thin-layer plates precoated with silica gel 60 using a mixture of ethyl acetate with isooctane (70:30 v/v) as solvent system. The radioactive zones of the plate are located, and the estrone peak is identified by comparison with an authentic standard. The corresponding band of silica gel is transferred to counting vials for detection with a liquid scintillation detector. Neither the substrate concentration nor the NADPH is rate limiting in this system. The number of counts emitted from estrone is calculated in the absence of the test compound and for each concentration of the test compound. The IC$_{50}$ values are determined graphically as the concentration of the test compound at which the counts pertaining to the amount of estrone formed is reduced to 50% of the control value.

With 5-p-cyanophenyl-5,6,7,8-tetrahydroimidazo[1,5-a]pyridine as representative test compound, an IC$_{50}$ of $4.5 \times 10^{-9}$M is obtained according to the method mentioned above.

The in vivo inhibition of aromatase activity of the compounds of the present invention can be demonstrated as follows:

Twenty-one-day-old female rats are injected subcutaneously with 10 IU pregnant mare serum gonadotropin (PMS). Two days later the same rats are injected subcutaneously with 30 IU human chorionic gonadrotropin (hCG). On the day following the hCG treatment the rats are injected subcutaneously with either propylene glycol (0.2 ml: p.o.) or with various doses of the 5-p-cyanophenyl-5,6,7,8-tetrahydroimidazo[1,5-a]pyridine as representative test compound. One hour later all of the rats are treated with 2.25 mg 4-androstene-3,17-dione in 0.1 ml oil, subcutaneously. Four hours after the injection of androstenedione the rats are killed and their ovaries removed and trimmed free of adhering tissue and stored in pairs at $-40°$ C. To determine the total estrogen content of the ovaries, 1.5 ml of 0.05M aqueous potassium phosphate buffer, pH 7.4, and 0.2 ml of 0.1N aqueous sodium hydroxide are added to the tissues which are then homogenized. The homogenate is extracted with 15 ml of diethyl ether, 5 ml aliquots are radioimmunoassayed with antiserum having 100% cross reactivity with estrone, estradiol and estriol. The results are expressed as ng estrogen/pair of ovaries.

When 5-p-cyanophenyl-5,6,7,8-tetrahydroimidazo[1,5-a]pyridine is tested as a representative compound for in vivo inhibition of aromatase activity according to the in vivo test described, supra, a statistically significant inhibition of estrogen synthesis is obtained at doses of 0.1, 0.05, and 0.025 $\mu$moles/100 g (P<0.05) as shown in the following Table:

TABLE

Suppression of Ovarian Estrogen Content of PMS-hCG Primed Rats by 5-p-cyanophenyl-5,6,7,8-tetrahydroimidazo[1,5-a]-pyridine Given 1 Hour Prior to Androstenedione (n 6/group)

| Dose $\mu$moles/100 g | Mean Ovarian Estrogen Content ng/pair of Ovaries + S.E. |
|---|---|
| 0 | 1.187 ± 0.044 |
| 0.1 | 0.072 ± 0.003 |
| 0.05 | 0.153 ± 0.013 |
| 0.025 | 0.194 ± 0.031 |

Surprisingly, while the test compound is found to be an effective aromatase inhibitor in vitro and in vivo, it apparently is devoid of cholesterol side-chain cleavage inhibitory activity in vivo, since it does not induce adrenal hypertrophy as verified by endrocrine organ evaluation.

Due to their pharmacological properties as aromatase inhibitors, the novel compounds of the formula Ia and Ib can be used as medicaments, for example in the form of pharmaceutical compositions, for the treatment of hormonal diseases, e.g. estrogen dependent tumours, especially mammary carcinoma, and anomalies, e.g. gynecomastia, in warm-blooded animals (humans and animals), by enteral, e.g. oral, or parenteral administration of therapeutically effective doses.

The use of these compounds as medicaments, especially with carcinostatic activity, in one of the methods referred to above for treatment of the human or animal body, also falls within the scope of the invention.

The daily doses of such compounds are from about 0.1 mg to 100 mg, preferably from 0.5 mg to about 50 mg/kg of body weight, for mammals, depending on the species, and also for persons, depending on age, individual condition and mode of application. For parenteral administration, e.g. intramuscular or subcutaneous injection, or intravenous infusion, the doses within this range are in general lower than in enteral, i.e. oral or rectal, administration. The compounds of the formula Ia and Ib are administered orally or rectally, preferably in dosage unit formulations such as tablets, dragees, capsules or suppositories, and parenterally in particular in the form of injectable solutions, emulsions or suspensions, or of infusion solutions.

The invention further relates to pharmaceutical compositions for enteral, e.g. oral or rectal, administration, or for parenteral administration, which compositions comprise a therapeutically effective amount of a compound of the formula Ia and Ib optionally together with a pharmaceutically acceptable carrier or mixture of carriers. Solid or liquid inorganic or organic substances are used as carriers. Appropriate dosage unit formulations, especially for peroral administration, e.g. dragees, tablets or capsules, preferably contain about 5 mg to 100 mg, most preferably about 10 to 50 mg, of a compound of the formula Ia or Ib, or of a pharmaceutically acceptable salt of such a compound which is capable of salt formation, together with pharmaceutically acceptable carriers.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or, if desired, disintegrators, such as the above mentioned starches, also carboxymethyl starch, crosslinked polyvinylpyrrolidone, agar, alginic acid or a salt thereof such as sodium alginate. Adjuncts are in particular glidants and lubricants, for example silica, talc, stearic acid or salts thereof such as magnesium stearate or calcium stearate, and/or polyethylene glycol. Dragee cores are provided with suitable coatings which can be resistant to gastric juices, using inter alia concentrated sugar solutions which may contain gum arabic, talc, polyvinylpyrrolidinone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropylmethylcellulose phthalate. Dyes or pigments can be added to the tablets or dragee coatings, for example to identify or indicate different doses of active ingredient.

Further pharmaceutical compositions for oral administration are dry-filled capsules made of gelatin and also soft sealed capsules consisting of gelatin and a plasticiser such as glycerol or soritol. The dry-filled capsules can contain the active ingredient in the form of granules, for example in admixture with fillers such as lactose, binders such as starches and/or glidants such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers can also be added.

Suitable pharmaceutical compositions for rectal administration are e.g. suppositories, which consist of a combination of the active ingredient with a suppository base. Examples of suitable suppository bases are natural or synthetic triglycerides, paraffin, polyethylene glycols and higher alkanols. It is also possible to use gelatin rectal capsules which contain a combination of the active ingredient with a base material. Suitable base materials are e.g. liquid triglycerides, polyethylene glycols and paraffins.

Particularly suitable dosage forms for parenteral administration are suspensions of the active ingredient, such as corresponding oily injection solutions or suspensions, for which are used suitable lipophilic solvents or vehicles such as fatty oils, for example sesame oil, or synthetic fatty acid esters, for example ethyl oleate or triglycerides, or aqueous injection suspensions or solutions uwhich contain substances which increase the viscosity, for example sodium carboxymethylcellulose, sorbitol and/or dextran, and optionally also stabilizers.

The pharmaceutical compositions of the present invention are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture of granulate, if desired or necessary after the addition of suitable adjuncts, to tablets or dragee cores.

The compounds of the formula Ia are prepared by the following process preferably by (a) Cyclizing a compound of the formula

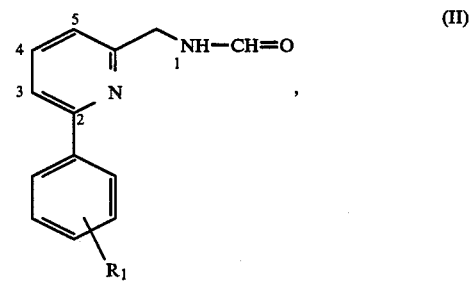

(II)

wherein $R_1$ is as defined above under formula Ia or the 4,5-dihydro derivative thereof, under acid conditions or, (b) For the preparation of the 7,8-dihydro derivative, cyclizing a compound of the formula

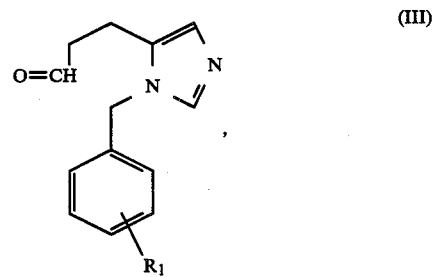

(III)

wherein $R_1$ is as defined above under formula Ia under basic conditions or (c) Converting in a compound of the formula

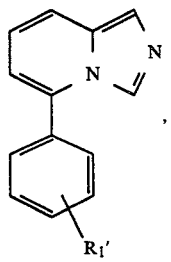
(IV)

wherein $R_1'$ is a group or radical that can be converted to the cyano group or in the 7,8-dihydro derivative thereof, $R_1'$ to cyano, and, if desired, converting a compound obtained into another compound of the invention and/or converting a salt obtained into the free compound or into another salt and/or converting a free compound having a salt-forming group into a salt.

The compounds of the formula Ib are prepared by the following process, preferably by (d) Cyclizing a compound of the formula

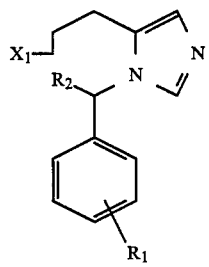
(V)

wherein $R_1$ and $R_2$ are as defined above under formula Ia and $X_1$ is a leaving group, in the presence of a base, or (e) Cyclizing a compound of the formula

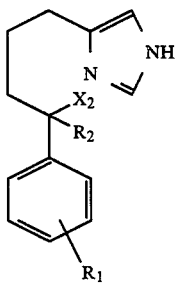
(VI)

wherein $R_1$ and $R_2$ are as defined above under formula Ia and $X_2$ is a leaving group, in the presence of a base, (f) Converting in a compound of the formula

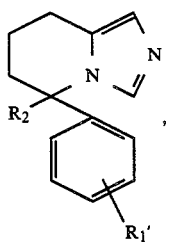
(VII)

wherein $R_1'$ is a group or radical that can be converted to the cyano group, $R_1'$ to cyano and, if desired, converting a compound obtained into another compound of the invention and/or converting a salt obtained into the free compound or into another salt and/or converting a free compound having a salt-forming group into salt and/or separating a racemic mixture obtained into the individual enantiomers.

Process (a)

The cyclization of the formylamino compound of the formula II is advantageously carried out under conditions such as described for the cyclization of 6-methyl-2-methylaminopyridine to 5-methylimidazo[1,5-a]pyridine in J. Org. Chemistry 40, 1210(1975). Said cyclization under acid conditions may be achieved advantageously with a Lewis acid, such as polyphosphoric acid, phosphorous oxychloride or polyphosphate ester.

Process (b)

The cyclization of the formyl compound of the formula III is carried out under basic conditions. The base employed in this process is any base that readily accepts protons, for example an amine, e.g. a tertiary amine such as a tri-lower alkylamine, e.g. trimethylamine or triethylamine, a cyclic tertiary amine such as N-methylmorpholine, a bicyclic amidine, e.g. a diazabicycloalkene such as 1,5-diazabicyclo[4.3.0]non-5-ene or 1,5-diazabicyclo[5.4.0]undec-5-ene (DBU), or is for example, a base of the pyridine type, e.g. pyridine. A suitable base is also an inorganic base, for example an alkali metal hydroxide or alkaline earth metal hydroxide, e.g. sodium, potassium or calcium hydroxide.

A preferred base is an alcoholate, for example an alkali metal alcoholate, for example sodium or potassium methylate, ethylate or tert-butylate.

The cyclization according to process (a) and (b) is generally carried out in organic inert solvents, such as suitable alcohols, such as methanol, ethanol or isopropanol, ketones, such as acetone, ethers, such as dioxan or tetrahydrofuran, nitriles, such as acetonitrile, hydrocarbons, such as benzene or toluene, halogenated hydrocarbons, such as methylene chloride, chloroform or carbon tetrachloride, esters, such as ethyl acetate, or amides, such as dimethylformamide or dimethylacetamide, and the like. The reaction temperature is between room temperature and the boiling temperature of the reaction mixture, preferably between 60° C. and the boiling temperature of the reaction mixture.

The cyclization is preferably carried out under inert gas atmosphere, preferably nitrogen atmosphere.

Process (c)

A group or radical $R_1'$ in a compound of the formula IV which can be converted into the —CN group is, for example, hydrogen, esterified hydroxy, for example halo, especially chloro, bromo, or iodo, or a sulfonyloxy group, for example p-toluenesulfonyloxy, benzenesulfonyloxy or mesyloxy, sulfo, amino, carboxy, carboxy in the form of a functional derivative, for example carbamoyl, lower alkylcarbamoyl, for example t-butylcarbamoyl, or haloformyl, for example chloro- or bromoformyl, formyl, a formyl group in the form of a functional derivative, for example hydroxyiminomethyl, or a halomagnesium group, for example iodo-, bromo- or chloromagnesium.

The conversion of a compound of the formula IV wherein $R_1'$ is hydrogen, to a compound of the formula Ia is performed according to the known method of C. Friedel, F. M. Crafts and P. Karrer by reacting with cyanogen chloride or bromide or according to the method of J. Houben and W. Fisher, by reacting with trichloroacetonitrile. The standard catalyst aluminum chloride is used in these reactions and hydrogen chloride or hydrogen bromide is split off, which can be removed from the reaction mixture after addition of a base, preferably an amine, for example triethylamine or pyridine.

The conversion of a compound of the formula IV wherein $R_1'$ is halo, for example chloro, bromo or iodo to a compound of the formula Ia is performed by using a cyanide salt, especially sodium or potassium cyanide or, preferably, copper(I) cyanide. Preferred solvents for this reaction are pyridine, quinoline, dimethylformamide, 1-methyl-2-pyrrolidinone and hexamethylphosphoric triamide. High temperatures, especially reflux temperatures of the reaction mixture are preferred.

The conversion of a compound of the formula IV wherein $R_1'$ is a sulfonyloxy group, for example p-toluenesulfonyloxy, benzenesulfonyloxy or mesyloxy, or is sulfo, to a compound of the formula Ia is performed by reaction with an alkali metal cyanide, preferably sodium or potassium cyanide. High temperatures, especially the reflux temperature of the reacton mixture, are preferred.

The conversion of a compound of the formula IV wherein $R_1'$ is amino to a compound of the formula Ia proceeds over several steps. Firstly, a diazonium salt is formed by reaction of the amino compound with an alkali nitrite salt, preferably potassium nitrite, according to the known reaction named after Sandmeryer. The diazonium salt can be reacted in situ with cuprous cyanide or a cyanide complex with labile cyano groups, preferably potassium cuproammonium cyanide or with catalytic amounts of freshly precipitated copper powder in the presence of an alkali metal cyanide, for example sodium or potassium cyanide. This reaction is referenced in detail in Houben-Weyl, Methoden der Organischen Chemie, Thieme Stuttgart 1952, Vol. VIII.

A carboxy group $R_1'$ can be converted to cyano by reaction with chlorosulfonylisocyanate according to the method of R. Graf, Angewandte Chemie Vol. 80, 183 (1968). Dimethylformamide is the preferred solvent, carbon dioxide is evolved and the chlorosulfonic acid-dimethylformamide addition salt is precipitated in this reaction.

The conversion of a compound of the formula IV wherein $R_1'$ is a carboxy group in the form of a functional derivative, for example carbamoyl, lower alkylcarbamoyl, for example t-butylcarbamoyl, to a compound of the formula Ia is performed with a strong dehydrating agent, such as phosphorus pentoxide, phosphoryl chloride, thionyl chloride, phosgene or oxalyl chloride.

A haloformyl group $R_1'$, for example chloro- or bromoformyl, is reacted with ammonia or a primary or secondary amine, for example methyl- or dimethylamine. The amide thus obtained is converted to the nitrile of the formula Ia, optionally in situ, with the dehydrating agents mentioned above, for example phosphorous pentachloride in case of the unsubstituted amide or phosphoryl chloride in case of a mono- or di-lower alkylated amide.

The dehydration is preferably carried out in the presence of a suitable base. A suitable base is, for example, an amine, for example a tertiary amine, for example tri-lower alkylamine, for example trimethylamine, triethylamine or ethyl diisopropylamine, or N,N-di-lower alkylaniline, for example N,N-dimethylaniline, or a cyclic tertiary amine, for example a N-lower alkylated morpholine, for example N-methylmorpholine, or is, for example, a base of the pyridine type, for example pyridine or quinoline.

The conversion of a formyl group to a cyano group is carried out by converting the formyl group to a reactive functional derivative, for example a hydroxyiminomethyl group, and converting this group to cyano by a dehydrating agent.

A suitable dehydrating agent is one of the inorganic dehydrating agents mentioned above, for example phosphorous pentachloride, or, preferably, the anhydride of an organic acid, for example the anhydride of a lower alkane carboxylic acid, for example acetic acid anhydride.

The conversion of the formyl group to hydroxyimino is carried out by reacting the starting material of formula IV wherein $R_1'$ is formyl with an acid addition salt of hydroxylamine, preferably the hydrochloride.

The starting material of the formula IV wherein $R_1'$ is formyl can be converted directly to a compound of the formula Ia by reaction with O,N-bis-(trifluoroacetyl)-hydroxylamine in the presence of a base, for example pyridine, according to the method of D. T. Mowry, Chem. Rev. 42, 251 (1948).

The conversion of a compound of the formula IV wherein $R_1'$ is a halomagnesium group, for example, iodo-, bromo-, or chloromagnesium, to a compound of the formula Ia is performed by reacting the magnesium halide with cyanogen halide or dicyanogen. Magnesium halide, for example magnesium chloride, or magnesium cyanohalide, for example magnesium cyanochloride, is produced. The "Grignard" compound of the formula IV wherein $R_1'$ is a halomagnesium group is prepared in a conventional manner, for example by reacting a compound of the formula IV wherein $R_1'$ is halo, for example chloro, bromo or iodo, in dry ether with magnesium.

Unless stated otherwise, the conversion of a compound of the formula IV to a compound of the formula Ia is preferably carried out in an inert, preferably anhydrous, solvent or solvent mixture, for example in a carboxylic acid amide, for example a formamide, for example dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally in the presence of an alcohol, for example methanol or ethanol, or water, optionally at reduced or elevated temperature, for example in a temperature range from approximately $-40°$ C. to appropximately $+100°$ C., preferably from room temperature to the boiling temperature of the reaction mixture and optionally under inert gas atmosphere, for example nitrogen atmosphere.

Process (d)

In a starting material of the formula V, a leaving group $X_1$ is preferably esterified hydroxy, for example lower alkanoyloxy, for example acetoxy, or mesyloxy, benzenesulfonyloxy or toluenesulfonyloxy, or, preferably, halogen, for example chlorine or bromine.

A suitable base is, for example an aqueous alkali metal or alkaline earth metal hydroxide solution, for example a sodium potassium or calcium hydroxide solution, a bicyclic amidine, for example 1,5-diazabicyclo[5.4.0]undec-5-ene, or preferably an alcoholate, for example sodium or potassium methylate, ethylate or tert-butylate.

The cyclisation is carried out in an aprotic organic solvent, for example in an ether, for example diethyl ether, dioxan or tetrahydrofuran, or ketone, for example acetone, an amide, for example dimethylformamide or hexamethylphosphoric acid triamide, or in a mixture thereof, optionally also in a mixture of the mentioned solvents with an alkane, for example n-hexane or petroleum ether. The reaction temperature is between approximately −50° and 50° C., preferably between −10° and room temperature. The reaction is preferably carried out under an inert gas atmosphere, for example an argon or nitrogen atmosphere.

Process (e)

In a starting material of the formula VI, a leaving group $X_2$ is preferably esterified hydroxy, for example lower alkanoyloxy, for example acetoxy, or mesyloxy, benzenesulfonyloxy or toluenesulfonyloxy, or, preferably, halogen, for example chlorine or bromine.

The cyclisation is carried out in a manner analogous to process (d) by using the same base, for example potassium-tert-butylate, and the same solvent, for example tetrahydrofuran.

Process (f)

In a starting material of the formula VII, the groups $R_1'$ that can be converted to the cyano group are defined as the group $R_1'$ in a starting material of the formula IV.

The conversion of $R_1'$ to cyano is carried out in a manner analogous to process (c) by using the same reagents and observing the same reaction conditions.

Subsequent Reactions

A compound of the formula Ia or the 7,8-dihydro derivative thereof can be converted to the corresponding 5,6,7,8-tetrahydro derivative of the formula Ib by reduction with hydrogen in the presence of an hydrogenation catalyst, e.g. platinum or palladium under acid conditions, for example in a mineral acid, for instance hydrochloric acid, or palladium charcoal at atmospheric pressure in an inert solvent, e.g. ethanol or ethyl acetate.

Salts of compounds of the formula Ia or Ib can be manufactured in a manner known per se. Thus, salts of compounds of the formula I can be formed in accordance with the method described in the Examples. Acid addition salts of compounds of the formula Ia or Ib are obtained in a customary manner, for example by treating the free compound with an acid or a suitable anion exchange reagent. Salts can be converted into the free compounds in a customary manner, for example by treating the acid addition salt with a suitable basic agent, for example an alcoholate, for example potassium-tert-butoxide.

Depending on the choice of starting materials and methods, the new compounds may be in the form of one of the possible isomers or mixtures thereof, for example, depending on the presence of chiral carbon atoms, as optical isomers, such as antipodes, or as mixtures of isomers, such as racemates or as diastereoisomers.

Resulting mixtures of diastereoisomers can be separated on the basis of the physicochemical differences of the constituents, for example by chromatography and/or fractional crystallisation.

Resulting racemates can furthermore be resolved into the optical antipodes by known methods, for example by recrystallisation from an optically active solvent, by means of microorganisms or by reacting an acidic intermediate or final product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates.

The invention further includes any variant of the present processes, in which an intermediate product obtainable at any stage thereof is used as starting material and the remaining steps are carried out, or the process is discontinued at any stage thereof, or in which the starting materials are formed under the reaction conditions or in which the reaction components are used in the form of their salts or optically pure antipodes. Mainly those starting materials should be used in said reactions, that lead to the formation of those compounds indicated above as being especially useful.

Preparation of the Intermediates

Compounds of the formula II are known or if they are novel, they can be prepared according to known methods, for example by reacting a compound of the formula

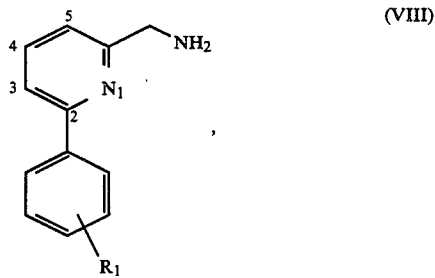

(VIII)

wherein $R_1$ is as defined above under formula Ia with formic acid or a reactive, functional derivative thereof.

A reactive, functional derivative of formic acid is, for example, formic acetic anhydride.

Compounds of the formula III are novel and are also subject matter of the present invention. They are prepared by reacting a compound of the formula V, wherein $X_1$ is hydroxy and $R_2$ is hydrogen, with dimethylsulfoxide in the presence of dehydrating agents, for example acid anhydrides, for example anhydrides of organic carboxylic acids, such as aliphatic or aromatic carboxylic acids or dicarboxylic acids, for example anhydrides of lower alkanecarboxylic acids, especially acetic acid anhydride, mixed anhydrides of lower alkane carboxylic or dicarboxylic acids with mineral acids, for example acetyl- or oxalylchloride, as well as anhydrides of inorganic acids, especially of phosphoric acid, such as phosphorus pentoxide. The above anhydrides, above all of organic carboxylic acids, for example oxalyl chloride, are preferably used in an approximately 1:1 mixture with dimethyl sulfoxide. Further dehydrating or water-absorbing agents are carbodiimides, above all dicyclohexylcarbodiimide, as well as diisopropylcarbodiimide, or keteneimides, for example diphenyl-N-p-tolylketeneimine; these reagents are preferably used in the presence of acid catalysts, such as phosphoric acid or pyridinium trifluoroacetate or pyridinium phosphate. Sulphur trioxide can also be used as a dehydrating or water-absorbing agent, in which case it is customarily employed in the form of a complex, for example with pyridine. A base is subsequently added, preferably a base which has been mentioned above under process (c), for example triethylamine.

Compounds of the formula IV, wherein $R_1'$ is hydrogen, esterified hydroxy, sulfo, amino, carboxy in the form of a functional derivative, formyl, formyl in the form of a functional derivative are novel and are also subject matter of the present invention.

The compounds of the instant invention have valuable pharmacological properties for example by inhibiting aromatase activity in mammals, including humans. For example, these compounds inhibit the metabolic conversion of androgens to estrogens. Thus, the compounds of formula IV are useful in the treatment of gynecomastia, i.e. male breast development, by inhibiting the aromatization of steroids in males susceptible to this condition. Moreover, the compounds of formula IV are useful in the treatment of estrogen dependent diseases, including estrogen dependent breast cancer, especially in postmenopausal females, by inhibiting estrogen synthesis.

These effects are demonstrable in in vitro assay tests of in vivo animal tests mentined above with respect to compounds of the formula Ia or Ib using advantageously mammals, e.g. guinea pigs, mice, rats, cats, dogs, or monkeys.

Due to their pharmacological properties as aromatase inhibitors, the novel compounds of the formula IV can be used as medicaments, for example in the form of pharmaceutical compositions, for the treatment of hormonal diseases, e.g. estrogen dependent tumours, especially mammary carcinoma, and anomalies, e.g. gynecomastia, in warm-blooded animals (humans and animals), by enteral, e.g. oral, or parenteral administration of therapeutically effective doses.

The use of these compounds as medicaments, especially with carcinostatic activity, in one of the methods referred to above for treatment of the human or animal body, also falls within the scope of the invention.

The same doses of the compounds of the formula IV are required for administration as mentioned above for the compounds of the formula Ia and Ib. Compounds of the formula IV are administered orally or rectally, preferably in dosage unit formulations such as tablets, dragees, capsules or suppositories, and parenterally in particular in the form of injectable solutions, emulsions or suspensions, or of infusion solutions.

The invention further relates to pharmaceutical compositions for enteral, e.g. oral or rectal, administration, or for parenteral administration, which compositions comprise a therapeutically effective amount of a compound of the formula IV optionally together with a pharmaceutically acceptable carrier or mixture of carriers. Solid or liquid, inorganic or organic, pharmaceutically acceptable materials which have been mentioned above, are used as carriers.

The compounds of the formula IV are prepared by the following process, preferably by (a') Cyclizing a compound of the formula

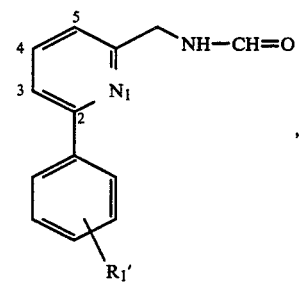

wherein $R_1'$ is as defined above under formula IV or the 4,5-dihydro derivative thereof, under acid conditions or (b') For the preparation of the 7,8-dihydro derivative, cyclizing a compound of the formula

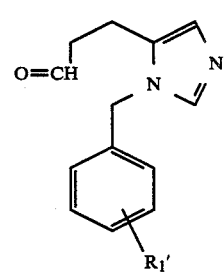

wherein $R_1'$ is as defined above under formula IV under basic conditions and, if desired, converting a compound obtained into another compound of the invention and/or converting a salt obtained into the free compound or into another salt and/or converting a free compound having a salt-forming group into a salt and/or separating a racemic mixture obtained into the individual enantiomers.

Process (a') and (b') are carried out in a manner analogous to processes (a) and (b) mentioned above.

Compounds of the formula V are known or if they are novel, they can be prepared according to known methods, for example by reacting a compound of the formula

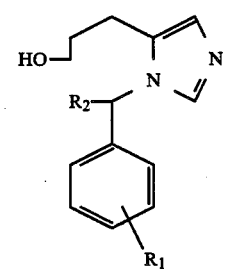

wherein $R_1$ and $R_2$ are as defined above under formula Ib with a halogenating agent or by esterifying the hydroxy with a reactive functional derivative of a sulfonic acid or carboxylic acid.

In a compound of the formula XI, $R_2$ is preferably hydrogen. The reaction of a compound of the formula XI with a halogenating agent, such as thionyl chloride or phosphorous pentachloride, is carried out in a manner analogous to the halogenation process as described in U.S. Pat. No. 4,089,955.

The reaction of a compound of the formula XI with a reactive functional derivative of a sulfonic or carboxylic acid, for example a mixed anhydride with a mineral acid, for example mesylchloride, benzenesulfonyl chloride or p-toluenesulfonylchloride, or acetyl chloride, is carried out by known esterification methods.

Compounds of the formula VI are known or if they are novel, they can be prepared according to known methods, for example by reacting a compound of the formula

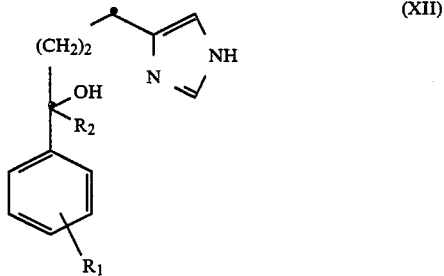

(XII)

wherein $R_1$ and $R_2$ are as defined above under formula Ib, with a halogenating agent or by esterifying the hydroxy group with a reactive, functional derivative of a sulfonic acid or a carboxylic acid. $R_2$ is preferably hydrogen.

The halogenation reaction is carried out analogously to the process according to U.S. Pat. No. 4,089,955.

The reaction of a compound of the formula XII with a reactive, functional derivative of a sulfonic or carboxylic acid, for example a mixed anhydride with a mineral acid, for example mesylchloride, benzenesulfonyl chloride or p-toluenesulfonylchloride, or acetyl chloride, is carried out by known esterification methods.

Compounds of the formula VII, wherein $R_1'$ is hydrogen, esterified hydroxy, sulfo, amino, carboxy in the form of a functional derivative, formyl, formyl in the form of a functional derivative are novel and are also subject matter of the present invention.

The compounds of the formula VII of the instant invention have valuable pharmacological properties for example by inhibiting aromatase activity in mammals, including humans. For example, these compounds inhibit the metabolic conversion of androgens to estrogens. Thus, the compounds of the formula VII are useful in the treatment of gynecomastia, i.e. male breast development, by inhibiting the aromatization of steroids in males susceptible to this condition. Moreover, the compounds of formula VII are useful in the treatment of estrogen dependent diseases, including estrogen dependent breast cancer, especially in postmenopausal females, by inhibiting estrogen synthesis.

These effects are demonstrable in in vitro assay tests or in vivo animal tests mentioned above with respect to compounds of the formula Ia or Ib using advantageously mammals, e.g. guinea pigs, mice, rats, cats, dogs, or monkeys.

Due to their pharmacological properties as aromatase inhibitors, the novel compounds of the formula VII can be used as medicaments, for example in the form of pharmaceutical compositions, for the treatment of hormonal diseases, e.g. estrogen dependent tumours, especially mammary carcinoma, and anomalies, e.g. gynecomastia, in warm-blooded animals (humans and animals), by enteral, e.g. oral, or parenteral administration of therapeautically effective doses.

The use of these compounds as medicaments, especially with carcinostatic activity, in one of the methods referred to above for treatment of the human or animal body, also falls within the scope of the invention.

The same doses of the compounds of the formuls VII are required for administration as mentioned above for the compounds of the formula Ia or Ib. Compounds of the formula VII are administered orally or rectally, preferably in dosage unit formulations such as tablets, dragees, capsules or suppositories, and parenterally, in particular in the form of injectable solutions, emulsions or suspensions, or infusion solutions.

The invention further relates to pharmaceutical compositions for enteral, e.g. oral or rectal, administration, or for parenteral administration, which compositions comprise a therapeutically effective amount of a compound of the formula VII optionally together with a pharmaceutically acceptable carrier or mixture of carriers. Solid or liquid inorganic or organic, pharmaceutically acceptable materials which have been mentioned above are used as carriers.

The compounds of the formula VII are prepared by the following process, preferably by (d") Cyclizing a compound of the formula

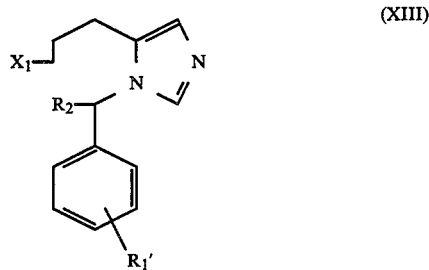

(XIII)

wherein $R_1'$ and $R_2$ are as defined above under formula Ib and $X_1$ is a leaving group, in the presence of a base, or (e") cyclizing a compound of the formula

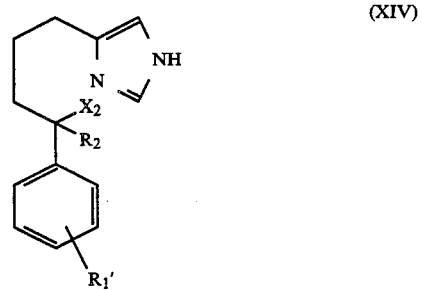

(XIV)

wherein $R_1'$ and $R_2$ are as defined above under formula Ib and $X_2$ is a leaving group, in the presence of a base, and, if desired, converting a compound obtained into another compound of the invention and/or converting a salt obtained into the free compound or into another salt and/or converting a free compound having a salt-forming group into a salt and/or separating a racemic mixture obtained into the individual enantiomers.

Compounds of the formula VIII are known or if they are novel, they can be prepared according to known methods, for example by hydrogenation of compound of the formula

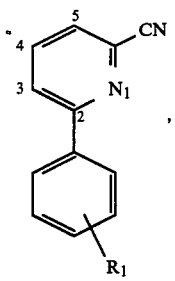 (XV)

wherein $R_1$ is as defined above under formula Ia.

The hydrogenation is preferably carried out in the presence of a catalyst, for example platinum or palladium on charcoal, in the presence of a mineral acid, for example hydrochloric acid.

Compounds of the formula IX are known or if they are novel, they can be prepared according to known methods, for example by reacting a compound of the formula

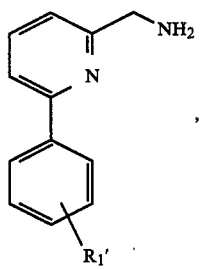 (XVI)

wherein $R_1'$ is as defined above under formula IV with formic acid or a reactive, functional derivative thereof.

Compounds of the formula X are known or if they are novel, they can be prepared according to known methods, for example by reacting a compound of the formula XIII, wherein $X_1$ is hydroxy, $R_1'$ is as defined above under formula Ib and $R_2$ is hydrogen, with dimethylsulfoxide in the presence of a dehydrating agent, for example oxalyl chloride.

This process is carried out in a manner analogous to the process for the preparation of compounds of the formula III.

Compounds of the formula XI are known or if they are novel, they can be prepared according to known methods, for example by reacting a compound of the formula

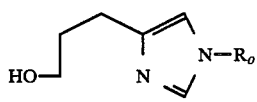 (XVII)

wherein $R_o$ is a blocking group, for example di-lower alkylated carbamoyl, for example dimethylcarbamoyl and the hydroxy group is protected by a conventional hydroxy protecting groups, for example trimethylsilyl, with a compound of the formula

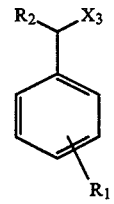 (XVIII)

wherein $R_2$ is as defined under formula Ib, preferably hydrogen, $R_1$ is as defined under formula Ia and $X_3$ is a leaving group, for example esterified hydroxy, for example halogen, for example chlorine or bromine, or sulfonyloxy, for example mesyloxy or p-toluene sulfonyloxy.

Compounds of the formula XII wherein $R_2$ is hydrogen are known or if they are novel, they can be prepared according to known methods for example by reacting a compound of the formula

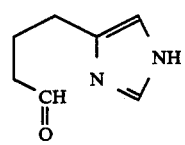 (XIX)

in an organometallic type reaction with a compound of the formula

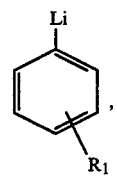 (XX)

wherein $R_1$ is as defined under formula Ia.

Compounds of the formula XIII and XIV can be prepared in a manner analogous to the compounds of the formula V and VI.

Compound of the formula XV can be prepared by converting a compound of the formula

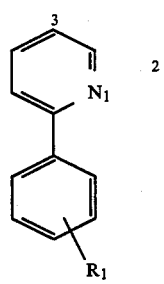 (XXI)

to the N-oxide with an oxidizing agent, e.g. peracetic acid, treating the N-oxide with a methylating agent, e.g. dimethyl sulfate and substituting the 2-position with a cyanide ion.

Compounds of the formula XVI can be prepared by catalytic hydrogenation of a compound of the formula

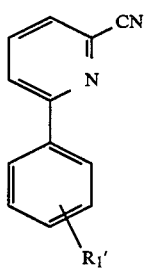

(XXII)

in a manner analogous to the preparation of compounds of formula VIII from compounds of the formula XV.

Compounds of the formulae XVII—XXI are known.

Compounds of the formula XXII can be prepared in a manner analogous to the preparation of compounds of the formula XV by using a compound of the formula

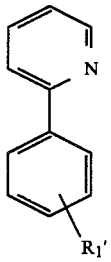

(XXIII)

as starting material which is known.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

5-p-Cyanophenyl-5,6,7,8-tetrahydroimidazo[1,5-a]pyridinehydrochloride

A solution of 8.1 g of 5-(3-chloropropyl)-1-p-cyanophenylmethyl-1H-imidazole in 50 ml of tetrahydrofuran is cooled to 0°. To this is added 7.0 g of potassium t-butoxide as a solid in portions. The mixture is stirred at room temperature for 2 hours, neutralized with 10% acetic acid and partitioned between methylene chloride and water. The organic layer is washed with water, dried over magnesium sulfate and evaporated to yield an oil which is dissolved in a small volume of acetone and neutralized with ethereal hydrogen chloride. On cooling, the title compound is obtained as a white solid. M.P. 201°–203°.

Preparation of the starting materials:

(a)
1-Dimethylcarbamoyl-4-trimethylsilyloxypropyl-1H-imdazole

To a suspension of 51.8 g of 4-(3-hydroxy-n-propyl)-1H-imidazole (obtainable according to Il Farmaco, Ed. Sc. 29, 309 (1973)) in 500 ml of acetonitrile 50.0 g of triethylamine is added. To this mixture 48.6 g of dimethyl carbamoyl chloride is added dropwise. When addition is complete, the mixture is refluxed for 21 hrs. The solution is cooled to 0°, whereupon there is precipitation of triethylamine hydrochloride. To this mixture is added 50.0 g of triethylamine followed by 54.0 g of chlorotrimethylsilane. After addition is complete stirring is continued for 1 hour. The mixture is diluted with an equal volume of ether and filtered. The filtrate is evaporated to an oil which is triturated with ether and filtered to remove additional triethylamine hydrochloride. This filtrate is then evaporated to yield the title compound (a) as an oil.

(b)
1-p-Cyanophenylmethyl-5-(3-hydroxypropyl)-1H-imidazole

A solution of 97.0 g of 1-dimethylcarbamoyl-4-trimethylsilyloxypropyl-1H-imidazole and 72.0 g of 1-bromomethyl-4-cyanobenzene in 500 ml of acetonitrile is refluxed for 10 hours. The solution is cooled to 0° in an ice bath and ammonia gas is bubbled in for a few minutes. The mixture is then evaporated in vacuo to give a semi-solid which is dissolved in 500 ml of 1N hydrochloric acid. The solution is allowed to stand at room temperature for 15 minutes and then is extracted with ether. The pH of the aqueous phase is adjusted to 9 with 50% sodium hydroxide solution and the mixture is then extracted with methylene chloride. The methylene chloride extracts are washed with water, dried over sodium sulfate and evaporated to give a semi-solid which is triturated with cold acetone to yield the title compound (b) as a white solid, m.p. 121°–123°.

(c)
5-(3-Chloropropyl)-1-p-cyanophenylmethyl-1H-imidazole

To a solution of 5.2 g of thionyl chloride in 80 ml of methylene chloride is added 8.4 g of 1-p-cyanophenylmethyl-5-(3-hydroxypropyl)-1H-imidazole as a solid in portions. The rate of addition is regulated to control the foaming that occurs. When addition is complete, the solution is refluxed for 1.5 hours, cooled in ice and filtered to obtain the hydrochloride salt of the title compound (c) as a buff-colored solid, m.p. 190°–191°.

The salt is partitioned between methylene chloride and saturated sodium bicarbonate solution. The organic extracts are washed with water, dried over sodium sulfate and evaporated to yield the free base as an oil.

EXAMPLE 2

5-p-Cyanophenyl-5,6,7,8-tetrahydroimidazo[1,5-a]pyridine hydrochloride

A solution of 2.0 g of 4-(4-chloro-4-p-cyanophenyl-n-butyl)-1H-imidazole in 50 ml of chloroform is refluxed for 4 hours under nitrogen, cooled and evaporated to yield the title compound.

Preparation of the starting materials:

(a) 4-(3-Formyl-n-propyl)-1-trimethylsilylimidazole

A solution of 1.82 g of 4-(3-ethoxycarbonylpropyl)-1H-imidazole in 30 ml of tetrahydrofuran under nitrogen is treated with 0.5 g of sodium hydride (50% oil dispersion) at 0° for 30 minutes and 1.45 ml of trimethylsilyl chloride at 0° for 3 hours. The reaction mixture is washed with cold 0.5N sodium bicarbonate solution, dried over sodium sulfate and evaporated to dryness. The oil is redissolved in 100 ml of methylene chloride at −78° under nitrogen and 12.82 ml of diisobutylaluminum hydride (1.56M) is added dropwise. The reaction mixture is stirred for 5 minutes at −78°, quenched with 1 ml of methanol followed by 10 ml of water and filtered through Celite ®. The organic phase is separated, dried over sodium sulfate and evaporated to yield the title compound (a).

(b) 4-(4-p-tert-Butylaminocarbonylphenyl-4-hydroxy-n-butyl)-1-trimethylsilylimidazole 6.95 g of p-tert-butylaminocarbonylbromobenzene is dissolved in 175 ml of tetrahydrofuran at −70° under nitrogen and 20.1 ml of a solution of n-butyllithium (2.7 m) in hexane is added dropwise. After reacting 30 minutes, a solution of 5.69 g of 4-(3-formyl-n-propyl)-1-trimethylsilyl imidazole in 10 ml of tetrahydrofuran is added slowly. The reaction mixture is allowed to warm slowly to room temperature and 20 ml of ammonium chloride is added. The organic layer is separated, dried over sodium sulfate and evaporated to yield the title compound (b).

(c) 4-(4-Chloro-4-p-cyanophenyl-n-butyl)-1H-imidazole

A solution of 4.5 g of 4-(4-p-tert-butylaminocarbonylphenyl-4-hydroxy-n-butyl)-1-trimethylsilylimidazole in 50 ml of thionyl chloride is refluxed for 1 hour, cooled and evaporated. The residue is partitioned between methylene chloride and aqueous sodium bicarbonate solution. The organic phase is separated, dried over sodium sulfate and evaporated to yield the title compound (c).

EXAMPLE 3

5-p-Cyanophenylimidazo[1,5-a]pyridine

A solution of 0.1 g of 5-p-tert-butylaminocarbonylphenylimidazo[1,5-a]pyridine in 3 ml of toluene is treated with 40 μl of phosphorus oxychloride at 90° for 5 hours. The solvent is evaporated and the residue is redissolved in 30 ml of chloroform at 0°. An ice-cold ammonium hydroxide solution is added and the organic phase is separated, dried over sodium sulfate and evaporated. The residue is chromatographed on silica with ethyl acetate to yield the title compound, m.p. 117°–118°.

Preparation of the starting material:

(a) 6-Cyano-2-p-ethoxycarbonylphenylpyridine 8.9 ml of 40% peracetic acid is added dropwise to 14.08 g of 2-(p-ethoxycarbonylphenyl)pyridine so as to maintain the reaction temperature between 80° and 85°. After the additon is complete the reaction mixture is heated at 90° for 3 hours, and allowed to cool to room temperature. The excess peracetic acid is destroyed with aqueous sodium sulfite solution. The solvent is evaporated and the residue taken up in methylene chloride and refiltered through celite ®. Evaporation yields 2-p-ethoxycarbonylphenylpyridine-N-oxide which is treated with 8.660 g dimethyl sulfate in 62 ml of toluene at 90° for 3 hours. The solvent is evaporated and the residue redissolved in an ice-cold mixture of 8 ml of water and 9.3 ml of 1N sodium hydroxide. A solution of 13.64 g of potassium cyanide in 10 ml of water is added slowly and the reaction mixture is maintained at 0° for 24 hours. Extraction with methylene chloride, drying over sodium sulfate and evaporation of solvent yields the title compound (a); IR (CH$_2$Cl$_2$) 2200 cm$^{-1}$.

(b) 6-Aminomethyl-2-p-ethoxycarbonylphenylpyridine 16.23 g of 6-cyano-2-p-ethoxycarbonylphenylpyridine is hydrogenated at atmosperic pressure in 254 ml of methanol with 12.9 ml of concentrated hydrochloric acid and 2.63 g of 10% palladium on charcoal until 2 molar equivalents of hydrogen have been consumed. Sodium methoxide (6.9 g) is added and the catalyst is filtered off. The solvent is evaporated. The residue is redissolved in 20 ml of methylene chloride and the salts are removed by filtration. Evaporation of the solvent yields a solid which is recrystallized from chloroform to yield the title compound (b) m.p. 141°–143°.

(c) 2-p-Ethoxycarbonylphenyl-6-formylaminomethylpyridine

A solution of 0.76 g 6-aminomethyl-2-p-ethoxycarbonylphenylpyridine in 10 ml of formic acid is heated at 90° for 15 hours. The reaction mixture is cooled to 0°, made basic with excess saturated ammonium hydroxide solution and extracted with chloroform. The organic extracts are dried and evaporated to yield the title compound (c) which is recrystallized from toluene, m.p. 119.5°–120.5°.

(d) 5-p-Ethoxycarbonylphenylimidazo[1,5-a]pyridine

A solution of 9.8 g of 2-p-ethoxycarbonylphenyl-6-formylaminomethylpyridine and 11.15 g phosphorus oxychloride in 26 ml of toluene is heated at 90° for 15 hours. The solvent is evaporated and the residue taken up in 50 ml of methylene chloride, cooled to 0° and made basic with excess ice-cold, saturated ammonium hydroxide solution. The organic phase is separated, dried and evaporated. The residual solid is passed through 100 g of silica gel with ethyl acetate as eluent to yield after crystallization the title compound (d), m.p. 118°–119°.

(e) 5-p-Carboxyphenylimidazo[1,5-a]pyridine

A solution of 1.18 g of 5-p-ethoxycarbonylphenylimidazo[1,5-a]pyridine in 10 ml of ethanol and 14 ml of 1N sodium hydroxide solution is refluxed for 3 hours, cooled and evaporated. The residue is partitioned between water and ethyl acetate. The aqueous phase is separated and adjusted to pH 5. The solid is filtered, washed with water and dried to yield the title compound (e), m.p. 308°–310° (dec.).

(f) 5-p-tert-Butylaminocarbonylphenylimidazo[1,5-a]pyridine

To a slurry of 0.4 g of 5-p-carboxyphenylimidazo[1,5-a]pyridine in 40 ml of methylene chloride under nitrogen at room temperature, is added 30 μl of N,N-dimethylformamide followed by 0.16 ml of oxalyl chloride. The reaction mixture is stirred until gas evolution is complete and 0.46 ml of tert-butylamine is added dropwise. Stirring is discontinued after 90 min. and 10 ml of saturated sodium bicarbonate solution is added. The organic layer is separated, dried over sodium sulfate and evaporated to yield the title compound (f), m.p. 128°–131°.

EXAMPLE 4

5-p-Cyanophenyl-5,6,7,8-tetrahydroimidazo[1,5-a]pyridine hydrochloride

A solution of 1.13 g of 5-p-carbamoylphenyl-5,6,7,8-tetrahydroimidazo[1,5-a]pyridine and 1.0 ml of phosphorus oxychloride in 30 ml of chloroform is refluxed for 15 hours, cooled and evaporated with toluene. The resulting oil is redissolved in 30 ml of methylene chloride, cooled to 0° and 30 ml of an ice-cold solution of 50% ammonium hydroxide solution is added. The organic phase is separated, dried and evaporated to an oil. Filtration through 20 g of silica with ethyl acetate yields the free title compound which is dissolved in 20 ml of acetone and treated with 1.2 ml of 3N ethereal hydrogen chloride to yield its hydrochloride, m.p. 209°–210°.

Preparation of the starting materials:

(a)
5-p-Ethoxycarbonylphenyl-5,6,7,8-tetrahydroimidazo[1,5-a]pyridine hydrochloride A solution of 2.0 g of 5-p-ethoxycarbonylphenylimidazo[1,5-a]pyridine in 120 ml of anhydrous ethanol containing 30 ml of concentrated hydrochloric acid, is hydrogenated with 1.0 g of 10% palladium on charcoal at 40 psi of hydrogen and 60° for 4 hours. The catalyst is filtered and the solvent is evaporated to yield a solid which is recrystallized from isopropanol and ether to provide the title compound (a), m.p. 164°–166°.

(b)
5-p-Carboxyphenyl-5,6,7,8-tetrahydroimidazo[1,5-a]pyridine

A solution of 0.66 g of 5-p-ethoxycarbonylphenyl-5,6,7,8-tetrahydroimidazo[1,5-a]pyridine in 8.0 ml of ethanol and 8.0 ml 1N sodium hydroxide is refluxed for 3 hours, cooled and evaporated. The residue is partitioned between water and ethyl acetate. The aqueous phase is adjusted to pH 5 with concentrated sulfuric acid and the solid is filtered and air-dried to yield the title compound (b), m.p. 309°–310° (dec.).

(c)
5-p-Carbamoylphenyl-5,6,7,8-tetrahydroimidazo[1,5-a]pyridine

A solution of 5.42 g of 5-p-carboxyphenyl-5,6,7,8-tetrahydroimidazo[1,5-a]pyridine in 75 ml of thionyl chloride is refluxed for 30 min, cooled and evaporated with toluene. The residue is redissolved in methylene chloride, cooled to 0° and treated with gaseous ammonia until the solution is saturated. The reaction mixture is stirred for 10 min. under an ammonia atmosphere and the resulting solid is collected by filtration to yield the title compound (c), m.p. 181°–183°. Treatment with a molar equivalent of fumaric acid in ethanol yields the fumarate salt, m.p. 164°–166° (dec.).

EXAMPLE 5

5-p-Tolyl-5,6,7,8-tetrahydroimidazo[1,5-a]pyridine hydrochloride

A solution of 0.36 g of 5-p-hydroxymethylphenylimidazo[1,5-a]pyridine in 25 ml of ethanol and 6.4 ml of concentrated hydrochloric acid is hydrogenated with 0.15 g of 10% palladium on charcoal at 40 psi of hydrogen and 60° L for 4 hours. The reaction mixture is filtered and evaporated and the residue is partitioned between methylene chloride and sodium bicarbonate solution. The organic phase is dried over sodium sulfate and evaporated to an oil which is purified by preparative layer chromatography on silica with ethyl acetate. The hydrochloride salt is prepared in acetone with 1.1 molar equivalents of ethereal hydrogen chloride to yield the title compound, m.p. 173°–175°.

Preparation of the starting material:

5-p-Hydroxymethylphenylimidazo[1,5-a]pyridine 1 g of 5-p-Ethoxycarbonylphenyl-imidazo[1,5-a]pyridine is dissolved in 26 ml of methylene chloride at −78° under nitrogen, 6.6 ml of diisobutylaluminum hydride in toluene (11.4 mmole) is added dropwise. After stirring for 1 hour, 1.5 ml of methanol is added, the cold bath is removed and 15 ml of water is added. The salts are filtered off, the organic phase is dried over sodium sulfate and evaporated to yield the title compound, m.p. 137°–138°.

EXAMPLE 6

5-p-Cyanophenyl-7,8-dihydroimidazo[1,5-a]pyridine

A solution of 0.24 g of 1-p-cyanophenylmethyl-5-(2-formylethy)-1H-imidazole in 10 ml of anhydrous ethanol is refluxed under nitrogen for 2 hours with 20 mg of potassium tert-butoxide, cooled and evaporated to yield the title compound.

Preparation of the starting material:

1-p-Cyanophenylmethyl-5-(2-formylethyl)-1H-imidazole

A solution of 0.14 ml of dimethylsulfoxide in 5 ml of methylene chloride is cooled to −78° under N$_2$ and 0.1 ml of oxalyl chloride is added dropwise. After 30 min, a solution of 0.24 g of 1-p-cyanophenylmethyl-5-(3-hydroxypropyl)-1H-imidazole in 1 ml of methylene chloride and 0.2 ml of dimethylsulfoxide is added slowly. The reaction mixture is stirred at −78° for 2 hours and 1 ml of triethylamine is added slowly. The reaction mixture is allowed to warm slowly to room temperature, diluted with 30 ml of methylene chloride and washed three times with 10 ml of water. The organic phase is dried over sodium sulfate and evaporated to yield the title compound as an oil, NMR (60 MHZ): $\delta$5.15 (S, 2H), 9.65 (S, 1H).

EXAMPLE 7

5-p-Cyanophenyl-5,6,7,8-tetrahydroimidazo[1,5-a]pyridine

A solution of 1.6 g of 5-p-cyanophenyl-7,8-dihydroimidazo[1,5-a]pyridine in 50 ml of ethyl acetate is hydrogenated at atmospheric pressure with 0.2 g of 5% palladium on charcoal until the theoretical uptake of hydrogen is complete. The catalyst is filtered, and the solvent evaporated to yield the title compound, m.p. 117°–118°.

EXAMPLE 8

5-p-Cyanophenyl-5,6,7,8-tetrahydroimidazo[1,5-a]pyridine

A solution of 54 mg of 5-p-cyanophenylimidazo[1,5-a]pyridine hydrochloride in 5.0 ml methanol is hydrogenated at room temperature and atmospheric pressure for 30 minutes with 0.1 g of 10% palladium on charcoal. The catalyst is filtered and 0.21 ml of 1N sodium hydroxide is added. The filtrate is evaporated, taken up in 10 ml of methylene chloride and filtered through Celite ®. Evaporation yields an oil which is chromatographed on silica gel with ethyl acetate to yield 5-p-cyanophenyl-5,6,7,8-tetrahydroimidazo[1,5-a]pyridine, m.p. 117°–118°.

EXAMPLE 9

5-p-Cyanophenyl-5,6,7,8-tetrahydroimidazo[1,5-a]pyridine

A mixture of 85 mg of 5-p-bromophenyl-5,6,7,8-tetrahydroimidazo[1,5-a]pyridine and 74 mg of cuprous cyanide in 1 ml of N,N-dimethylformamide is heated under nitrogen at 120° for 11 hours. The reaction mixture is cooled, diluted with 10 ml of water and extracted with ethyl acetate. The organic extracts are dried over sodium sulfate and evaporated. The resulting oil is chromatographed on silica gel with ethyl acetate to yield the title compound, m.p. 117°–118°.

Preparation of the starting materials:

(a)
1-p-Bromobenzyl-5-(3-hydroxypropyl)-1H-imidazole

A solution of 11.2 g of 1-dimethylcarbamoyl-4-(3-trimethylsilyloxypropyl)-1H-imidazole and 12.49 g of p-bromobenzyl bromide in 110 ml of acetonitrile is refluxed for 24 hours. The solution is cooled to 0° and ammonia gas is bubbled through the reaction mixture for 5 minutes. After reacting an additional 45 minutes at room temperature, the solvent is evaporated. The residue is taken up in 100 ml of 1N hydrochloric acid and extracted with 50 ml of ether. The aqueous phase is adjusted to pH 8 and extracted with ethyl acetate (5×50 ml). The organic extracts are washed with water, dried over sodium sulfate and evaporated. The resulting oil is chromatographed on 530 g of silica gel with ethyl acetate:methanol:saturated NH$_4$OH (90:5:5) to yield the title compound (a) as an oil; NMR: $\delta$5.00 (s, 2H).

(b) 1-p-Bromobenzyl-5-(3-chloropropyl)-1H-imidazole 1-p-Bromobenzyl-5-(3-hydroxypropyl)-1H-imidazole is treated with thionyl chloride analogous to the method described in example (1c) to give the title compound (b).

(c)
5-p-Bromophenyl-5,6,7,8-tetrahydroimidazo[1,5-a]pyridine

A solution of lithium diisopropylamide, prepared at 0° from 0.12 ml of diisopropylamine and 0.33 ml of n-butyllithium (2.5M) in 2 ml of tetrahydrofuran under nitrogen, is added to a solution of 0.13 ml of N,N,N',N'-tetramethylethylene diamine and 0.124 g of 5-(3-chloropropyl)-1-p-bromobenzyl-1H-imidazole in 2 ml of tetrahydroduran at −78°. The reaction mixture is stirred for 3.5 hours, quenched at −78° with saturated ammonium chloride solution and extracted with methylene chloride (3×10 ml). The organic extracts are dried over sodium sulfate and evaporated to yield the title compound (c) which is purified by conversion to the hydrochloride salt.

EXAMPLE 10

5-p-Cyanophenyl-5,6,7,8-tetrahydroimidazo[1,5-a]pyridine

A solution of 2.01 g of 5-p-formylphenyl-5,6,7,8-tetrahydroimidazo[1,5-a]pyridine and 0.96 g of hydrazoic acid in 30 ml of benzene is maintained by external cooling at room temperature, while 0.8 ml of concentrated sulfuric acid is added dropwise. The reaction mixture is stirred for 2 hours and neutralized. The organic phase is separated, dried over sodium sulfate and evaporated to yield an oil which is chromatographed on silica gel with ethyl acetate to yield the title compound.

Preparation of the starting materials:

(a)
5-p-Hydroxymethylphenyl-5,6,7,8-tetrahydroimidazo[1,5-a]pyridine

A solution of 0.40 g of 5-p-ethoxycarbonylphenyl-5,6,7,8-tetrahydroimidazo[1,5-a]pyridine in 20 ml of methylene chloride is cooled to −70° under nitrogen and 4.0 ml of a 1.53M diisobutylaluminum hydride solution in toluene, is added dropwise. The reaction mixture is allowed to warm to room temperature, quenched with 3.2 ml of methanol and 15 ml of water and filtered through Celite ®. The layers are separated, the organic layer is dried over sodium sulfate and evaporated to yield the title compound (a), m.p. 142°–145°.

(b)
5-p-Formylphenyl-5,6,7,8-tetrahydroimidazo[1,5-a]pyridine

A solution of 0.16 ml of dimethylsulfoxide in 16 ml of methylene chloride is cooled to −70° under nitrogen and 0.17 g of oxalyl chloride is added dropwise. The reaction mixture is stirred for 30 min. and 0.24 g of 5-p-hydroxymethylphenyl-5,6,7,8-tetrahydroimidazo[1,5-a]pyridine is added slowly in 4 ml of methylene chloride. The reaction mixture is stirred for 2 hrs at −70°, 0.8 ml of triethylamine is added dropwise, and the reaction mixture is allowed to warm slowly to room temperature. The reaction mixture is diluted with 20 ml of methylene chloride, washed with water, dried over sodium sulfate and evaporated to yield the title compound (b) which is purified by conversion to the fumaric acid salt.

EXAMPLE 11

5-p-Cyanophenyl-5-methylthio-5,6,7,8-tetrahydroimidazo[1,5-a]pyridine hydrochloride A solution of lithium diisopropylamide is prepared at 0° under nitrogen, from 0.6 ml of n-butyllithium (2.5M) and 0.15 g of diisopropylamine in 5 ml of dry tetrahydrofuran and is transferred to 0.29 g of 5-p-cyanophenyl-5,6,7,8-tetrahydroimidazo[1,5-a]pyridine in 10 ml of tetrahydrofuran at −78°. The reaction mixture is stirred for 30 minutes and 0.14 g of dimethyl disulfide is added dropwise. Cooling is discontinued after 30 minutes and the reaction mixture is allowed to warm to room temperature and quenched with 10 ml of saturated ammonium chloride solution. The layers are separated and the organic phase is washed with cold 1N hydrochloric acid. The aqueous phase is neutralized and extracted with ethyl acetate. The organic extracts are dried over sodium sulfate and evaporated to an oil which is chromatographed on silica gel with 5% isopropanol in ethyl acetate. The resulting oil is redissolved in acetone and treated with 0.1 ml of 4N ethereal hydrogen chloride to yield the title compound, m.p. 204°–205°.

EXAMPLE 12

5-p-Cyanophenyl-5-ethoxycarbonyl-5,6,7,8-tetrahydroimidazo[1,5-a]pyridine

In a manner analogous to that described in example 11, reaction of 5-p-cyanophenyl-5,6,7,8-tetrahydroimidazo[1,5-a]pyridine with ethyl chloroformate yields the title compound.

EXAMPLE 13

5-p-Cyanophenyl-5,6,7,8-tetrahydroimidazo[1,5-a]pyridine

A solution of 1.65 g of 5-p-cyanophenyl-5-ethoxycarbonyl-5,6,7,8-tetrahydroimidazo[1,5-a]pyridine in 10 ml of methanol containing 0.2 g of sodium hydroxide is stirred for 3 hours at room temperature and 5 ml of 1N hydrochloric acid is added. The reaction mixture is refluxed for 1 hour, cooled and evaporated. The residue is partitioned between water and ethyl acetate. The organic layer is separated, dried over sodium sulfate and evaporated to yield the title compound.

EXAMPLE 14

5-p-Cyanophenyl-5,6,7,8-tetrahydroimidazo[1,5-a]pyridine

A solution of 2.13 g of 5-p-aminophenyl-5,6,7,8-tetrahydroimidazo[1,5-a]pyridine in 4 ml of concentrated hydrochloric acid and 10 ml of water is cooled in an ice-bath and a solution of 0.78 g of sodium nitrite in 2 ml of water is added slowly. The solution is added via dropping funnel to an ice cooled solution of 3.0 g of copper (I) cyanide in 10 ml of water, keeping the temperature between 30°–40°. The reaction is heated on a steam bath for 1 hour, cooled and brought to pH 9. The organic extracts are dried over sodium sulfate and evaporated and the residue is chromatographed on silica gel with ethyl acetate to yield the title compound.

Preparation of the starting material:

(a)
5-p-Aminophenyl-5,6,7,8-tetrahydroimidazo[1,5-a]pyridine

A solution of 2.42 g of 5-p-carboxyphenyl-5,6,7,8-tetrahydroimidazo[1,5-a]pyridine in 100 ml of ethylene dichloride is treated with 6 ml of concentrated sulfuric acid. The reaction mixture is heated to 40° and 6 ml of hydrazoic acid (2M in ethylene dichloride) is added dropwise. When gas evolution has ceased, the reaction is evaporated. The residue is redissolved in water and adjusted to pH 10. The aqueous phase is extracted with methylene chloride (3×30 ml). The organic extracts are dried over potassium carbonate and evaporated to yield the title compound (a).

EXAMPLE 15

Preparation of 10,000 tablets each containing 10 mg of the active ingredient:

Formula 5-p-Cyanophenyl-5,6,7,8-tetrahydroimidazo[1,5-a]pyridine: 100.00 g
Lactose: 2,535.00 g
Corn starch: 125.00 g
Polyethylene glycol 6,000: 150.00 g
Magnesium stearate: 40.00 g
Purified water: q.s.

All the powders are passed through a screen with openings of 0.6 mm. Then the drug substance, lactose, magnesium stearate and half of the starch are mixed in a suitable mixer. The other half of the starch is suspended in 65 ml of water and the suspension is added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave uppers bisected.

Analogously tablets are prepared containing the other compounds disclosed and exemplified herein.

EXAMPLE 16

Preparation of 1,000 capsules each containing 20 mg of the active ingredient:

Formula 5-p-Cyanophenyl-5,6,7,8-tetrahydroimidazo[1,5-a]pyridine: 20.0 g
Lactose: 207.0 g
Modified starch: 80.0 g
Magnesium stearate: 3.0 g Procedure All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 310 mg of said mixture each, using a capsule filling machine.

Analogously capsules are prepared, containing the other compounds disclosed and exemplified herein.

What is claimed is:

1. A compound of the formula

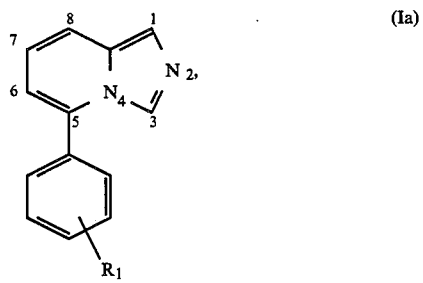

(Ia)

wherein $R_1$ represents cyano, nitro or $C_1$–$C_4$-alkyl, or a 7,8-dihydro derivative thereof, or a 5,6,7,8-tetrahydro compound of the formula

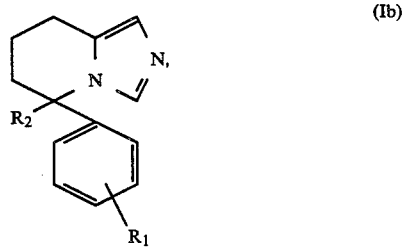

(Ib)

wherein $R_1$ is cyano, nitro or $C_1$–$C_4$ alkyl; and $R_2$ is hydrogen, $C_1$–$C_4$-alkyl, phenyl-$C_1$–$C_4$-alkyl, halogen, $C_1$–$C_4$-alkoxy, $C_1$–$C_4$-alkylthio, phenyl-$C_1$–$C_4$-alkylthio, phenylthio, hydroxy or mercapto esterified by $C_1$–$C_4$-alkanoyl, carboxy-$C_1$–$C_4$-alkyl, $C_1$–$C_4$-alkoxycarbonyl-$C_1$–$C_4$-alkyl, or $C_1$–$C_4$-alkanoyl; or a pharmaceutically acceptable salt thereof.

2. A compound according to claim 1 of the formula Ia wherein $R_1$ represents cyano, or a 7,8-dihydro derivative thereof, or a 5,6,7,8-tetrahydro compound of the formula Ib wherein $R_1$ is cyano and $R_2$ is hydrogen, $C_1$–$C_4$-alkyl, $C_1$–$C_4$-alkoxy, $C_1$–$C_4$-alkylthio, phenyl- $C_1$–$C_4$-alkylthio, phenylthio, or $C_1$–$C_4$-alkanoyl; or a pharmaceutically acceptable acid addition salt thereof.

3. A compound of the formula

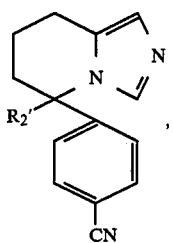
(Ic)

wherein $R_2'$ is hydrogen, $C_1$–$C_4$-alkyl, $C_1$–$C_4$-alkoxy, $C_1$–$C_4$-alkylthio, phenyl-$C_1$–$C_4$-alkylthio, phenylthio or $C_1$–$C_4$-alkanoyl; or a pharmaceutically acceptable acid addition salt thereof.

4. A compound according to claim 3 of the formula Ic wherein $R_2'$ is hydrogen being 5-p-cyanophenyl-5,6,7,8-tetrahydroimidazo[1,5-a]pyridine or a pharmaceutically acceptable salt thereof.

5. A compound according to claim 2 of the formula Ia being 5-p-cyanophenylimidazo[1,5-a]pyridine or a pharmaceutically acceptable acid addition salt thereof.

6. An aromatase inhibiting pharmaceutical composition comprising an effective aromatase inhibiting amount of a compound of claim 1 of the formula Ia or Ib, or a pharmaceutically acceptable salt thereof; together with a pharmaceutically acceptable carrier or a mixture of pharmaceutically acceptable carriers.

7. An aromatase inhibiting pharmaceutical composition according to claim 6 comprising an effective aromatase inhibiting amount of 5-p-cyanophenyl-5,6,7,8-tetrahydroimidazo[1,5-a]pyridine or a pharmaceutically acceptable salt thereof together with a pharmaceutically acceptable carrier or a mixture of pharmaceutically acceptable carriers.

8. A method of inhibiting aromatase activity in mammals which comprises administering to a mammal in need thereof an effective aromatase inhibiting amount of a pharmaceutical composition of claim 6.

9. A method of inhibiting aromatase activity in mammals which comprises administering to a mammal in need thereof an effective aromatase inhibiting amount of a pharmaceutical composition comprising an effective aromatase inhibiting amount of a compound according to claim 3 of the formula

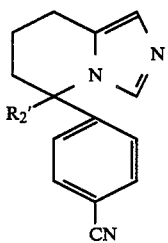
(Ic)

wherein $R_2'$ is hydrogen, $C_1$–$C_4$-alkyl, $C_1$–$C_4$-alkoxy, $C_1$–$C_4$-alkylthio, phenyl-$C_1$–$C_4$alkylthio, phenylthio or $C_1$–$C_4$-alkanoyl; or a pharmaceutically acceptable acid addition salt thereof; together with a pharmaceutically acceptable carrier or a mixture of pharmaceutically acceptable carriers.

10. A method according to claim 9 of inhibiting aromatase activity in mammals, which comprises administering to a mammal in need thereof an effective aromatase inhibiting amount of a pharmaceutical composition comprising an effective aromatase inhibiting amount of 5-p-cyanophenyl-5,6,7,8-tetrahydroimidazo[1,5-a]pyridine or a pharmaceutically acceptable acid addition salt thereof; together with a pharmaceutically acceptable carrier or a mixture of pharmaceutically acceptable carriers.

11. A method of inhibiting estrogen synthesis in mammals which comprises administering to a mammal in need thereof an effective aromatase inhibiting amount of 5-p-cyanophenyl-5,6,7,8-tetrahydroimidazo [1,5-a]pyridine or of a pharmceutically acceptable salt thereof or of a pharmaceutical composition comprising an effective aromatase inhibiting amount of a said compound together with a pharmaceutically acceptable carrier or a mixture of pharmaceutically acceptable carriers.

12. A compound of the formula

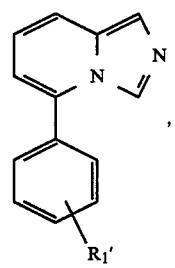
(IV)

wherein $R_1'$ is hydrogen, halo, sulfo, amino, carboxy, carbamoyl, lower alkylcarbamoyl, formyl or hydroxyiminoethyl; or a pharmaceutically acceptable salt thereof.

13. A compound of claim 12 being 5-p-tert-butylaminocarbonylphenylimidazo[1,5-a]pyridine.

14. An aromatase inhibiting pharmaceutical composition comprising an effective aromatase inhibiting amount of a compound of claim 12 together with a pharmaceutically acceptable carrier or a mixture of pharmaceutically acceptable carriers.

15. A method of inhibiting aromatase activity in mammals which comprises administering to a mammal in need thereof an effective aromatase inhibiting amount of a pharmaceutical composition of claim 14.

16. A compound of the formula

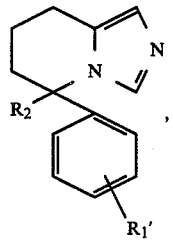
(VII)

wherein $R_1'$ is hydrogen, halo, sulfo, amino, carboxy, carbamoyl, lower alkylcarbamoyl, formyl or hydroxyiminoethyl; $R_2$ is hydrogen, $C_1$–$C_4$-alkyl, phenyl-$C_1$–$C_4$-alkyl, halogen, $C_1$–$C_4$-alkoxy, $C_1$–$C_4$-alkylthio, phenyl-$C_1$–$C_4$-alkylthio, phenylthio, hydroxy or mercapto esterified by $C_1$–$C_4$-alkanoyl, carboxy-$C_1$–$C_4$- alkyl, $C_1$–$C_4$-alkoxycarbonyl-$C_1$–$C_4$-alkyl, or $C_1$–$C_4$-alkanoyl; or a pharmaceutically acceptable salt thereof.

17. A compound according to claim 16 being 5-p-bromophenyl-5,6,7,8-tetrahydroimidazo[1,5-a]pyridine or a pharmaceutically acceptable salt thereof.

18. A compound of claim 16 being 5-p-carbamoylphenyl-5,6,7,8-tetrahydroimidazo[1,5-a]pyridine; or a pharmaceutically acceptable salt thereof.

19. An aromatase inhibiting pharmaceutical composition comprising an effective aromatase inhibiting amount of a compound of claim 16 together with a pharmaceutically acceptable carrier or a mixture of pharmaceutically acceptable carriers.

20. A method of inhibiting aromatase activity in mammals which comprises administering to a mammal in need thereof an effective aromatase inhibiting amount of a pharmaceutical composition of claim 19.

* * * * *